United States Patent
Benelli et al.

(10) Patent No.: US 11,707,561 B2
(45) Date of Patent: Jul. 25, 2023

(54) ANOTHER INSERT PIECE FOR A BLOOD TUBING SET TO PROMOTE MIXING AN INFUSION SOLUTION WITH A FURTHER FLUID

(71) Applicant: Fresenius Medical Care Deutschland GmbH, Bad Homburg (DE)

(72) Inventors: Davide Maria Benelli, Crema (IT); Massimo Earl Fini, Mirandola (IT); Reinhold Reiter, Crema (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 748 days.

(21) Appl. No.: 16/625,577

(22) PCT Filed: Jun. 27, 2018

(86) PCT No.: PCT/EP2018/067277
§ 371 (c)(1),
(2) Date: Dec. 20, 2019

(87) PCT Pub. No.: WO2019/002382
PCT Pub. Date: Jan. 3, 2019

(65) Prior Publication Data
US 2021/0402073 A1 Dec. 30, 2021

(30) Foreign Application Priority Data
Jun. 28, 2017 (EP) ..................... 17178458

(51) Int. Cl.
*A61M 1/36* (2006.01)
*A61M 1/16* (2006.01)
(Continued)

(52) U.S. Cl.
CPC ........ *A61M 1/3621* (2013.01); *A61M 1/1621* (2014.02); *A61M 1/3455* (2013.01);
(Continued)

(58) Field of Classification Search
CPC .............. A61M 1/3621; A61M 1/3627; A61M 5/1408; A61M 5/1409; A61M 39/02
See application file for complete search history.

(56) References Cited

U.S. PATENT DOCUMENTS

| 3,511,238 A | 5/1970 | Wrangell |
| 4,802,650 A * | 2/1989 | Stricker .............. A61M 5/1408 251/117 |

(Continued)

FOREIGN PATENT DOCUMENTS

| CN | 1874803 | 12/2006 |
| CN | 101631498 | 1/2010 |

(Continued)

OTHER PUBLICATIONS

International Preliminary Report on Patentability in Application No. PCT/EP2018/067277, dated Dec. 31, 2019, 12 pages.

(Continued)

*Primary Examiner* — Laura A Bouchelle
(74) *Attorney, Agent, or Firm* — Fish & Richardson P.C.

(57) ABSTRACT

The present invention relates to an insert piece for a blood tubing set that includes a first connection site for connecting a first tubing portion of the blood tubing set to the insert piece; a second connection site for connecting a second tubing portion of the blood tubing set to the insert piece; a third connection site for connecting a third tubing portion of the blood tubing set to the insert piece; a first main line for conducting a first liquid through the insert piece; a second main line for conducting the first liquid through the insert piece; a secondary line for conducting a second liquid into at least one of the first main line, and the second main line; and a connection portion which connects both main lines to each other or to the second connection site.

19 Claims, 13 Drawing Sheets

(51) Int. Cl.
*A61M 1/34* (2006.01)
*A61M 5/14* (2006.01)

(52) U.S. Cl.
CPC ........ *A61M 1/3496* (2013.01); *A61M 5/1413* (2013.01); *A61M 2206/14* (2013.01)

(56) References Cited

U.S. PATENT DOCUMENTS

| | | | |
|---|---|---|---|
| 5,306,265 | A | 4/1994 | Ragazzi |
| 7,556,060 | B2 * | 7/2009 | Guala ................... A61M 39/24 |
| | | | 137/895 |
| 7,931,612 | B2 | 4/2011 | Rosenblatt |
| 8,915,892 | B2 * | 12/2014 | Klewinghaus .... B01F 25/43141 |
| | | | 604/246 |
| 2010/0168643 | A1 | 7/2010 | Frugier et al. |
| 2010/0217232 | A1 | 8/2010 | Rosenblatt |
| 2013/0028788 | A1 | 1/2013 | Gronau et al. |
| 2013/0150772 | A1 | 6/2013 | Farnan et al. |
| 2014/0050614 | A1 | 2/2014 | Klewinghaus |
| 2016/0030656 | A1 | 2/2016 | Eikelmann et al. |

FOREIGN PATENT DOCUMENTS

| | | |
|---|---|---|
| CN | 102548521 | 7/2012 |
| CN | 102869331 | 1/2013 |
| CN | 104613232 | 5/2015 |
| CN | 105120918 | 12/2015 |
| CN | 105214158 | 1/2016 |
| DE | 4240681 | 6/1994 |
| DE | 102010047747 | 4/2012 |
| EP | 0165519 | 12/1985 |
| EP | 1666078 | 6/2006 |
| EP | 2183004 | 5/2010 |
| WO | WO 2005/042059 | 5/2005 |
| WO | WO 2007/101064 | 9/2007 |
| WO | WO 2008/101025 | 8/2008 |
| WO | WO 2009/030973 | 3/2009 |
| WO | WO 2010/109449 | 9/2010 |
| WO | WO 2011/039306 | 4/2011 |
| WO | WO 2011/125303 | 10/2011 |
| WO | WO 2014/026771 | 2/2014 |
| WO | WO 2015/000934 | 1/2015 |
| WO | WO 2016/206804 | 12/2016 |
| WO | WO 2018/055091 | 3/2018 |

OTHER PUBLICATIONS

International Search Report and Written Opinion in Application No. PCT/EP2018/067277, dated Jul. 26, 2018, 15 pages.

* cited by examiner

ANOTHER INSERT PIECE FOR A BLOOD TUBING SET TO PROMOTE MIXING AN INFUSION SOLUTION WITH A FURTHER FLUID

CROSS-REFERENCE TO RELATED APPLICATION

The present application is the national stage entry of International Patent Application No. PCT/EP2018/067277, filed on Jun. 27, 2018, and claims priority to Application No. EP 17178458.0 filed in Europe on Jun. 28, 2017, the disclosures of which are expressly incorporated herein in its entirety by reference thereto.

TECHNICAL FIELD

The present disclosure relates to an insertion piece, an extracorporeal blood tubing set, and a blood treatment apparatus.

BACKGROUND

During the extracorporeal blood treatment, infusion solutions or medicaments are mostly infused through the extracorporeal blood circuit, i.e., the utilized blood tubing system. Depending on the type of the infusion solution, a fast mixing of the infusion solution with the blood may be favorable or desirable. For example, anticoagulation infusion solutions are regularly infused during an extracorporeal blood treatment to prevent a possible occlusion of the extracorporeal blood circuit.

Two methods are mainly used for this purpose; the system and the regional anticoagulation. A citrate solution, which complexes calcium, and thus suppresses the blood coagulation, is mostly used as an anticoagulant in the regional anticoagulation. Prior to returning blood to the patient, an additional calcium must be substituted, since too-low calcium concentrations influence nerves and muscles, the blood coagulation and functions of lung, heart and kidneys. In the regional anticoagulation, a calcium-containing solution, by which the physiological calcium concentration in the system blood may be maintained, is therefore added to the blood before reinfusing it into the patient.

Infusing infusion solutions or medicaments into the tubing set of the extracorporeal blood circuit usually takes place through addition sites with a T-form (so-called "Tees"). Laminar flow conditions predominate in these Tees due to the circular cross section and the smooth inner wall at the addition site. In addition, the flow rates of the infused solutions are typically low in comparison with the blood flow.

The largely laminar flow conditions and the low flow rates of the infusion solutions or medicaments flowing into the blood stream may delay or slow down the mixing of the blood with the added infusion. This slow mixing of both liquids at the addition site is undesirable, especially when adding the calcium solution to blood, and may lead to clot problems at the addition site, due to the punctually continued higher calcium concentrations in blood. To prevent that, a fast and homogenous mixing of the added calcium solution with the blood is desirable. The same problem may however also occur when mixing other liquids, e.g. medicaments, the fast mixing of which may as well be advantageous.

In order to solve this problem, special addition sites, which have means for generating turbulences, have been described in the prior art. For example, an insert piece in form of a T-piece having a spiral structure for a blood tubing set is thus described in WO 2014/026771 A1. The spiral structure serves generating turbulences in the area of the infusion site. The turbulences serve or contribute to a better mixing of the fluids which are brought together.

Furthermore, there are solutions which generate a pulsed infusion flow of the infusion solution into the blood through intermittent operation of an infusion pump.

SUMMARY

This disclosure describes an apparatus for promoting mixing of an infusion solution with a further fluid, such as blood.

This disclosure describes an insert piece, an extracorporeal blood tubing set, and a blood treatment apparatus.

An insert piece is described herein as being intended to be inserted into a blood tubing set (or into a blood tubing system or an extracorporeal blood circuit) or to be part thereof, respectively. The insert piece disclosed herein can include at least a first connection site for connecting a first tubing portion of the blood tubing set to the insert piece. The insert piece disclosed herein can include a second connection site for connecting a second tubing portion of the blood tubing set to the insert piece. The insert piece disclosed herein can include a third connection site for connecting a third tubing portion of the blood tubing set to the insert piece. The insert piece disclosed herein can include a first main line for conducting a first liquid, preferably blood, through the insert piece. The first main line is in fluid communication with at least the first connection site and with the second connection site or with a lumen surrounded or formed by the first connection site and/or the second connection site.

The insert piece can include at least a second main line for conducting the first liquid, preferably blood, through the insert piece. Like the first main line, the second main line is also in fluid communication with the first connection site and with the second connection site.

The insert piece can include at least one secondary line for conducting, directly or indirectly, a second liquid, preferably an infusion solution, into at least one of the first main line, the second main line and a connection portion which connects both the first main line and the second main line to each other and/or to the second connection site.

The secondary line is in fluid communication with the third connection site or with a lumen surrounded or delimited by the third connection site.

The first connection site can include a perfusable or flow-through lumen having a first cross sectional area. The second connection site can include a perfusable or flow-through lumen having a second cross sectional area. At least one of the first main line and the second main line can include a perfusable lumen having a third cross sectional area. The secondary line includes a lumen portion. The lumen portion of the secondary line can include at least one opening or outlet opening for the second fluid.

The blood tubing set, extracorporeal blood circuit or the blood tubing system described herein includes at least one insert piece according to the present disclosure.

In some embodiments, the insert piece described herein is pressed or interposed between tubing portions of the blood tubing set or is integrally manufactured therewith.

In some embodiments, the insert piece described herein is fixed to at least one of the tubing portions of the blood tubing set. In some embodiments, the insert piece described herein is releasably connected to at least one of the tubing portions of the blood tubing set.

In some embodiments, the blood treatment apparatus is connected to at least one blood tubing set.

Embodiments described herein may encompass one or several of the aforementioned or following features in any desired combination unless the skilled person finds a particular combination as technically impossible.

Whenever numerical words are mentioned herein, the person skilled in the art shall recognize or understand them as indications of numerical lower limits. Unless it leads the person skilled in the art to an evident contradiction, the person skilled in the art shall comprehend the specification's use of "one" as encompassing "at least one". This understanding is also equally encompassed by the present invention as the interpretation that a numeric word, for example, "one" may alternatively mean "exactly one", wherever this is evidently technically possible to a person skilled in the art. Both interpretations are encompassed by the present disclosure and apply to all numerical words used herein.

Spatial information herein, such as "top", "bottom", etc., refer, in case of doubt, to the illustration as seen in the accompanying figures and as the position of the device in question when being used by one skilled in the art.

References to a cross section or cross sectional area of an element (such as a line) herein, may refer to the only cross section/cross sectional area, just one cross section/cross sectional area, the average one, the one in the middle section of the element, or the prevailing one.

In some embodiments, the first connection site, the second connection site, and/or the connection portion include a mostly cylindrical inner wall or a section having a cylindrical inner wall.

In some embodiments, the insert piece is manufactured integrally with the blood tubing set. All or some of the sections of the insert piece denoted herein as connection sites are in such embodiments passage sections between the insert piece and adjacent or continuing tubing portions.

In some embodiments, the secondary line is connected in fluid communication with, or includes, a source of infusion solution.

In some embodiments, the infusion solution is a calcium solution or includes a calcium solution. The present disclosure is however not limited to using a calcium-containing solution. Other medicament solutions are encompassed by the present disclosure, such as citrate solution.

In some embodiments, the third cross sectional area is, as a maximum, half, or substantially half, as large as the first cross sectional area and/or the second cross sectional area. For example, the third cross sectional area may be between 35% and 65% the first cross sectional area and/or the second cross sectional area. All intermediate values and in particular each integer percentage value (36%, 37%, 38%, etc.) are included or contemplated as well.

In some embodiments, the cross sectional area of the first main line and the cross sectional area of the second main line taken together (or their sum) are smaller than the cross sectional area of the first connection site, the second connection site and/or the cross sectional area of the tube section of the blood tube set connected to the insert piece. With this design, the flow of the first liquid can be accelerated within the first and/or the second main line, which in turn can contribute to generating turbulences and to preventing poor mixing.

In some embodiments, the cross sectional area of the first main line and the cross sectional area of the second main line taken together (or their sum) equal the cross sectional area of the first connection site, the cross sectional area of the second connection site and/or the cross sectional area of the tube section of the blood tube set connected to the insert piece. With this design, turbulences may be avoided upon entry of the fluid into the first main line and the second main line. However, turbulences are generated further downstream upon entry of the second fluid into the first fluid at the mouth or opening of the secondary line. Such turbulences achieved as intended can be used to prevent poor mixing.

The entrance into the first main line and/or into the second main line can optionally be tapered or otherwise define a decreased or decreasing cross section. A tapered cross section (or cross sectional area, which terms may be used interchangeably) can cause disturbance in the flow of the first liquid and result in turbulences. Turbulences, in turn, can contribute to an enhanced mixing of the first and the second liquids further downstream. The same applies optionally to the exit from the first main line and/or from the second main line.

Also, the cross sections need not to be increased or increasing or decreased or decreasing by deviations from, e. g., a circular cross section or need not be homogeneously altered along their entire circumference. Rather, amending only a portion of the circumference of the first main line and/or second main line can lead to the desired turbulences.

In some embodiments, a baffle or deflector element is provided in the interior area of the connection portion. The baffle or deflector element is arranged such that a second liquid flowing out of the outlet opening or opening of the secondary line is limited in its radial movement or in its movement in the outlet direction.

In some embodiments, the baffle or deflector element is not the inner wall of the main line, for example in the area of the first connection site, of the second connection site, or the connection portion.

In certain embodiments, an addition line is connected in fluid communication to a blood return line and/or to a blood withdrawal line of the blood tubing set via the secondary line of the insert piece or is connected to the insert piece.

In some embodiments, the blood tubing set is suitable and/or configured for executing a regional anticoagulation.

In some embodiments, the blood tubing set is suitable and/or configured for executing a hemodialysis, a hemofiltration, or a hemodiafiltration or a plasmapheresis treatment or a whole blood adsorption treatment.

In some embodiments, the connection portion is arranged—in flow direction of the first liquid—between the first main line and/or the second main line and the second and/or the third connection site. Hence, in some embodiments, the connection portion is arranged downstream of the first and/or the second main line. In some embodiments, the connection portion is arranged upstream of the second and/or the third connection site.

In some embodiments, the connection portion comprises, in a flow direction towards the second connection site or upstream of the second connection site, a cross section, in particular a conical cross section, which widens, increases or enlarges along the flow direction.

In some embodiments, a through-opening of the insert piece is arranged between, delimited by, or framed by sections of the first main line and sections of the second main line.

In some embodiments, the through-opening has a round, oval, or oblong hole form or shape. Alternatively, the through-hole includes a section which has a round, oval, or oblong hole form.

In some embodiments, the insert piece includes two or more components, which are welded and/or glued to each other. For example, the tubes may be glued or welded to the insert piece. In some embodiments, the insert piece includes, for example, an upper part and a lower part which are optionally glued one to one another. Alternatively, or additionally, the upper part and lower part of the insert piece may be interconnected to each other by other methods, such as clamping.

In some embodiments, the insert piece is integrally formed, for example by injection molding. The tubes may optionally be clamped and/or glued to the insert piece. Also, a welding process may be used for this purpose.

In some embodiments, at least one of the first main line and/or the second main line, or sections thereof, are tubes or channels.

The first main line and/or the second main line can be inserted into or integral with tube intakes or connectors, which are in fluid communication with the first connection site or with the second connection site, and which are optionally integrally produced therewith.

In some embodiments, at least one of the first main line and the second main line are integral parts of the insert piece.

In some embodiments, the insert piece is made of plastic. In some embodiments, the insert piece is made of injection molded plastic.

In some embodiments, the insert piece has no three-dimensional spiral structure for generating turbulences, in particular does not have a recessed section in the inner wall of the connection portion.

In some embodiments, the first, the second and/or the third connection site is bonded or connected to a tubing portion.

In some embodiments, the blood tubing set includes at least one of a drip chamber, further insert pieces in form of Tees or injection points, and the like.

When liquids are mentioned herein, it is not to be understood restrictively. The present invention encompasses or contemplates also bringing together other fluids in a wider sense.

In some embodiments, the first main line and the second main line have two common junction portions or connection positions, e. g. the first and the second connection sites. In some embodiments, the lumen of the first main line and the lumen of the second main line are physically separated from each other. For example, in some implementations, there are walls or other elements that separate the flow through the first main line from the flow through the second main line such that the fluid flowing through the first main line does not mix with the fluid flowing through the second main line. In some embodiments, the lumen of the first main line and the lumen of the second main line are separated at least along the majority of both the first main line and the second main line, i.e., the first main line and the second main line are separated though their lumens are in fluid communication with each other at both a first end section and a second end section of both the first main line and the second main line, respectively. The end sections may be the entrances into and the exits from the first main line and the second main line.

In some embodiments, the first main line and the second main line are arranged such that fluid can flow either through the first main line or through the second main line, e. g. since the fluid paths of the first and the second main lines are arranged in parallel one to the other, or next or besides to each other, but not in sequence or one following the other.

In some embodiments, neither the first main line nor the second main line includes a pressure-responsive valve.

In some embodiments, the insert piece does not include a flow regulator for controlling the flow through the insert piece or through the first or the second main line, in particular the insert piece does not include a flow regulator adjustable by the user, more specifically a thumb-wheel-regulator.

In some embodiments, the secondary line is in fluid communication with the lumen of the first main line, the second main line and/or the connection portion. Hence, the first liquid and the second liquid can be mixed by the insert piece.

In some embodiments, the first main line and the second main line define a common plane perpendicular to the main extension direction of the secondary line.

In some embodiments, both the first connection site and the second connection site extend along a common straight line. For example, the common straight line along which the first connection site and second connection site can coincide with the direction of the fluid flowing into and/or out from the insert piece.

In some embodiments, the cross section of any line, e. g. the first main line or the second main line, refers to the inner cross section or the perfusable cross section of a nose or another flexible tubing that is inserted or will be inserted into the corresponding first, second or third connection site.

In some embodiments, the cross section of the first tubing portion and/or of the first connection site is smaller than the cross section of the second tubing portion or of the second connection site.

In some embodiments, the first fluid enters through the first connection site of the insert piece during use.

In some embodiments, the second connection site is closer to the secondary line than the first connection site.

In some embodiments, the cross section of the first main line and/or of the second main line is bigger than, or equals, 50% of the cross section of the first tubing portion or of the first connection site.

In some embodiments, the sum of the cross sections of the first main line and of the second main line is bigger than the cross section of the first tubing portion or of the first connection site.

In some embodiments, the cross section of the first main line and the cross section of the second main line taken together equal the cross section of the first tubing portion or of the first connection site.

In some embodiments, the first main line and the second main line are arranged such that they form a circle within a plane, the plane preferably extending through the first and the second main line.

In certain embodiments, blood entering the insert piece through the first connection site is split into two flows through the first main line and the second main lines. The flows are separated from each other by the design of the first and second main lines and rejoin again, preferably near the outlet of the secondary line. That way, turbulences are created within the fluid flow in the insert piece.

In some embodiments, the first and the second main lines are arranged such that the separate flows through the first main line and the second main line collide or meet in a more or less frontal direction comparable to a frontal impact between the two flows.

In some embodiments, the secondary line and/or the third connection site are perpendicular to a plane along which the first and the second main lines extend. The opening plane (or mouth) of the secondary line, through which the second fluid exits in order to mix with the first fluid, can also be perpendicular to the plane along which the first and the second main lines extend. In some embodiments, the direction along which the second fluid exits from the secondary line in order to mix with the first fluid may be parallel to or part of the plane along which the first and the second main lines extend.

In some embodiments, the second fluid provided by the secondary line has to change its travelling direction inside of the mouth piece of the secondary line in order to exit from the secondary line and enter into the first fluid.

In some embodiments, the secondary line and/or the third connection site is perpendicular to the plane along the first and the second main lines extend. The opening plane (or mouth) of the secondary line, through which the second fluid exits in order to mix with the first fluid can be parallel to the plane along which the first and the second main lines extend; alternatively, the direction along which the second fluid exits from the secondary line in order to mix with the first fluid can be perpendicular to the plane along which the first and the second main lines extend.

In certain embodiments, the second fluid provided by the secondary line does not have to change its travelling direction inside of the mouth piece of the secondary line in order to exit from the secondary line and enter into the first fluid.

The effect of the design according to the present invention was tested by the inventors under the following simulation conditions:

A "blood solution of 1.5 l H$_2$O and 0.5 l Glycerol having a density of 1063.4 kg/m$^3$ and a viscosity of 0.3536 Pas was used. A "Calcium solution" of H$_2$O having a density of 997.561 kg/m$^3$ and a viscosity of 8.8871e-4 Pas was used.

The software used for simulation was "Hypermesh-ANSA" and "Star CCM+".

The speed of the flow for the solutions was 50 ml/min for the "blood" substitute solution and 10 ml/hour for the "Calcium" substitute solution.

At different sections (orthogonal planes at the axis of the outlet tube with differing distance to the outlet opening or mouth), the flow distribution of the tracer (calcium) was calculated with the formula below. The section of the tube is considered as a mesh, formed by i-th cells:

$$\gamma = 1 - \frac{\sum Ai \cdot \sqrt{(Vi - Vmin)^2}}{2 \cdot Vmin \cdot A}$$

Wherein:
$\gamma$: Tracer distribution
Ai: Area of the single i-th cell of the section
A: Total area of the section
Vi: Volumetric fraction of the solution of calcium, calculated in the single generic cell i
Vmin: Minimum value of the volumetric fraction on the Calcium solution in the section If Vi is similar to Vmin (therefore Vi−Vmin tends to 0) then the volumetric fraction of calcium is similar in all i cells of the section, which allows for a good mixing result.

If $\gamma$ tends to 1 a complete mixing of the tracer (calcium) is assumed.

If $\gamma$ tends to 0 no mixing of the tracer (calcium) has taken place.

The surface uniformity/tracer distribution computed by means of the above formula was: 0.71 at a site 0.5 cm downstream from where the "Calcium solution" was introduced into the "blood", 0.84 at a site 1 cm downstream, 0.88 at a site 2 cm downstream, 0.91 at a site 3 cm downstream, 0.93 at a site 4 cm downstream, 0.95 at a site 5 cm downstream, 0.96 at a site 6 cm downstream from where the "Calcium solution" was introduced into the "blood".

Some or all of the embodiments according to the present disclosure may include one or several of the aforementioned or following advantages.

One advantage is that the risk of blood clots resulting from improper mixing of the first and the second fluids can be minimized. Hence, the treatment need not to be interrupted because of clotting and/or occlusions.

In addition, due to the particular shape or design of the insert piece described herein, no additional devices or method steps are required for ensuring a swirling of the infusion solution with the blood. An accelerated and reliable mixing of the infusion solution with the blood may be achieved using the device described herein.

An advantage of using the insert piece according to the present disclosure is that the herein described advantages can be achieved without requiring a change in the controlling of the blood treatment apparatus or the pump for the infusion solution. Rather, the structure of the insert piece effects an advantageous distribution of the second fluid into the first fluid without requiring, e. g., a pulsating addition as described in, e. g., DE 10 2013 011 010 A1. The fluid mixing effect according to the present disclosure may be achieved by the geometry of the insert piece described herein alone. In particular, no amendments to the controlling of the infusion pump are required. Its conveying characteristics may be maintained. As a result, no structural or other type of adjustment of the blood treatment apparatus, e. g. a software adjustment or modification, is required to effectuate mixing of the solutions. Switching to using the insert pieces or blood tubing sets as described herein from extracorporeal blood treatment is easily accomplished since the insert pieces and blood tubing sets are single-use articles or disposables.

The effect of the insert piece according to the present disclosure is independent of parameters of the blood treatment. For example, if the conveying rate of the blood pump and the conveying rate of the pump for the infusion solution being in line with the former are changed, then the effect principle or the effect of the insert piece according to the present disclosure remains unchanged or undisturbed.

Also, as stated above, the design of the insert piece according to the present disclosure allows for a thorough mixing of the second fluid introduced into the first fluid. As a result, the second fluid can be used in a higher concentration because the increased mixing can result in no or less adverse effects, even when the second fluid, such as a calcium solution, is used in a relatively high concentration. Also, due to the good mixing features of the insert piece according to the present disclosure, the second fluid may be introduced at comparably low speed.

In addition, the insert piece has an extremely simple and, when desired, even symmetrical design, which allows the insert piece to be produced using simple injection molding tools, which may reduce the total costs of its production significantly.

DETAILED DESCRIPTION

Figure 1:
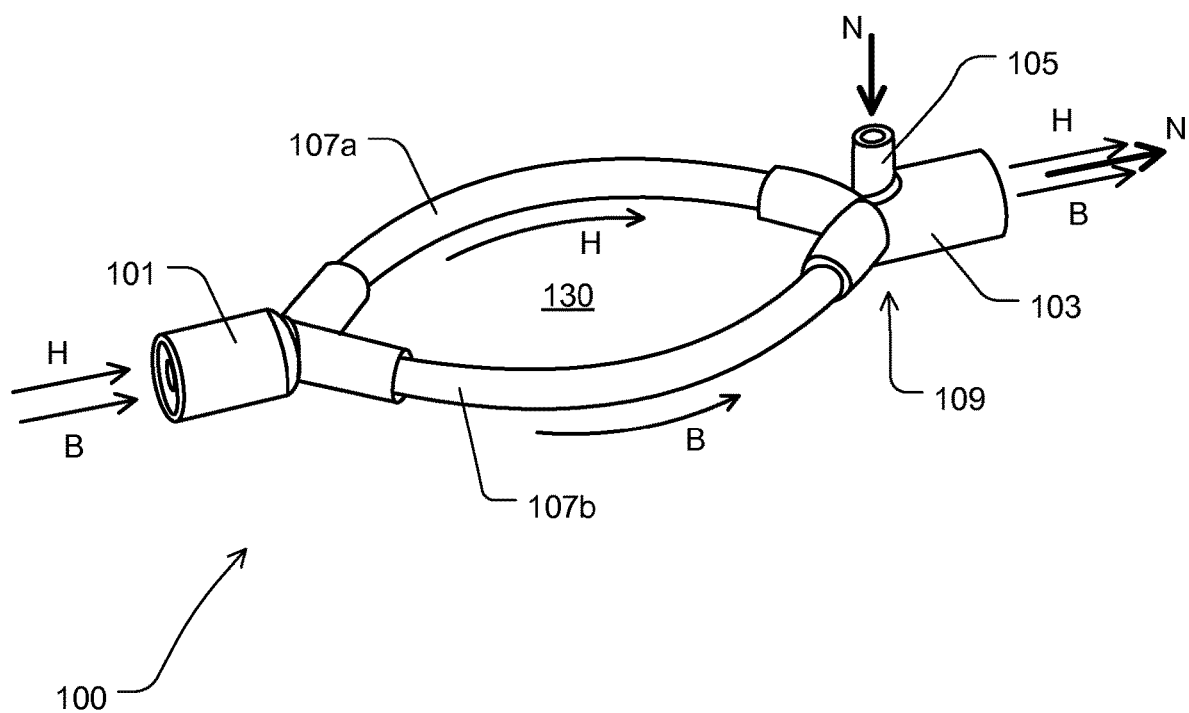
FIG. 1 shows an insert piece in a first exemplary embodiment.
Figure 11:
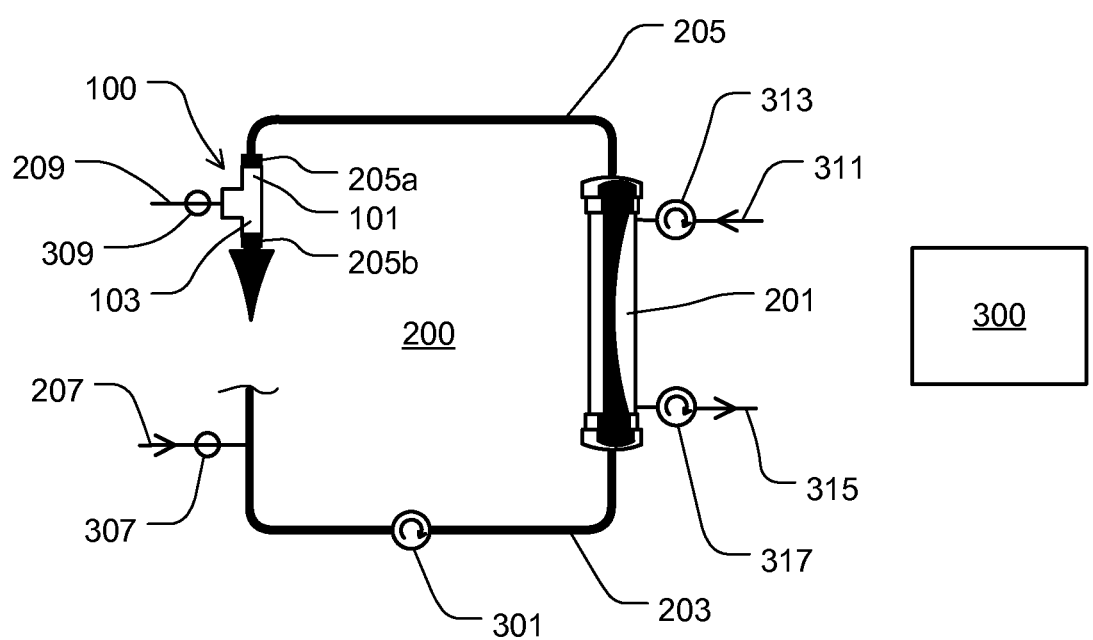
FIG. 11 shows a blood tubing set according to the present disclosure having an insert piece according to the present disclosure.

FIG. 1 shows an insert piece 100 in a first exemplary embodiment according to the present invention for a blood tubing set, such as the blood tubing set 200 of FIG. 11).

As depicted in FIG. 1, insert piece 100 includes a first connection site 101 configured to couple a first tubing portion 205a (see FIG. 11) of the blood tubing set 200 to the insert piece 100.

The insert piece 100 also includes a second connection site 103 configured to couple a second tubing portion 205b (see FIG. 11) of the blood tubing set 200 to the insert piece 100.

The insert piece 100 comprises a third connection site 105 configured to couple a third tubing portion, such as a line 209 for calcium solution of the blood tubing set 200 (see FIG. 11), to the insert piece 100.

The insert piece 100 comprises a first main line 107a for conducting a first liquid, such as blood, through the insert piece 100. The first main line 107a is in fluid communication with the first connection site 101 and the second connection site 103. The first liquid may flow in direction of the arrows H depicted in FIG. 1 into and through the first main line 107a.

The insert piece 100 also includes a second main line 107b for conducting the first liquid through the insert piece 100. The second main line 107b is in fluid communication with the first connection site 101 and the second connection site 103. The first liquid may flow in direction of the arrows B as depicted in FIG. 1 into and through main line 107b. In some embodiments, the insert piece includes three, four, or more main lines for conducting the first liquid through the insert piece 100.

The insert piece 100 includes an optional junction portion 109 (also referred to herein as a connection portion), in which the first main line 107a, the second main line 107b and a secondary line 111 (see FIG. 3) of the insert piece converge. As depicted in FIG. 1, the second connection site 103 and/or the third connection site 105 may form part of the junction portion 109.

Figure 3:
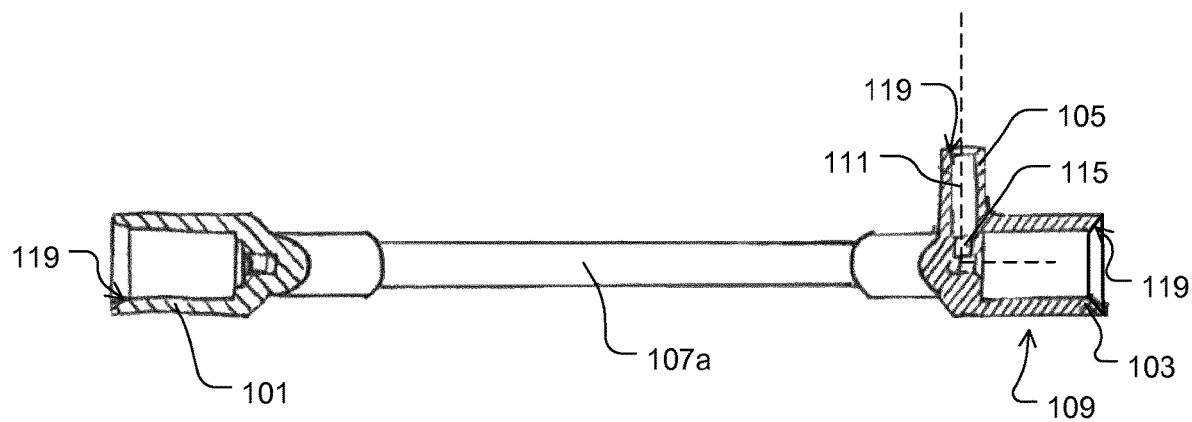
FIG. 3 shows a cross sectional view of the insert piece of FIG. 1 along a second plane.

As depicted in FIG. 3, insert piece 100 includes a secondary line 111. The secondary line 111 is configured to conduct a second liquid, preferably an infusion solution. The second liquid may flow in direction of the arrow N into the secondary line 111, as depicted in FIG.

The secondary line 111 is in fluid communication with the third connection site 105, and the secondary line 111 can be part of or end with the third connection site 105, as depicted in FIG. 1. The secondary line 111 is further in fluid communication with the first and the second main lines 107a, 107b.

The first connection site 101 defines a perfusable lumen having a first cross sectional area.

The second connection site 103 defines a perfusable lumen having a second cross sectional area.

The first and/or the second main lines 107a, 107b can define a perfusable lumen having a third cross sectional area.

The secondary line 111 defines a lumen which protrudes or opens into the interior of the junction portion 109 and which includes at least one opening or outlet opening 115. The second liquid conducted through the secondary line 111 and through the outlet opening 115 can be introduced into a lumen defined by the junction portion 109 or into the lumen defined by another line.

As FIG. 3 further shows, the lumen defined by the secondary line opens into and is fluidly coupled to the interior of the junction portion 109.

Figure 2:
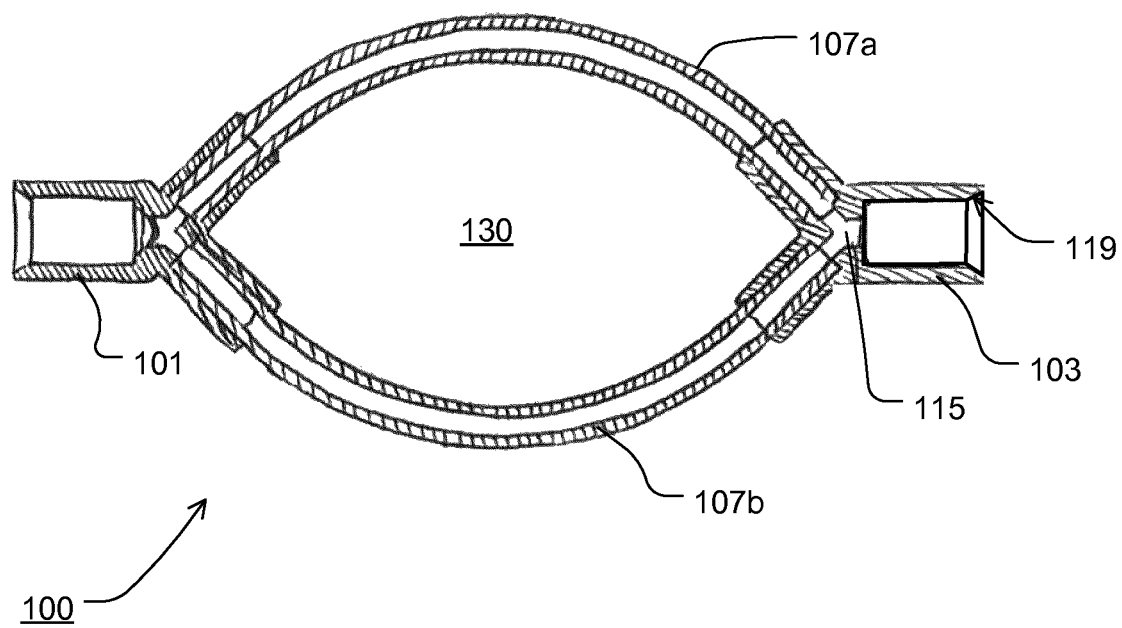
FIG. 2 shows a cross sectional view of the insert piece of FIG. 1 along a first plane.

The first connection site 101, the second connection site 103 and/or the third connection site 105 can each optionally include a chamfer 119 in the inner wall or of the outer wall of the respective connection site as depicted in FIGS. 2 and 3.

As depicted in FIG. 1, the first and the second main lines 107a, 107b together can, form an optional through-opening 130 of the insert piece 100.

Hence, blood entering the insert piece 100 through the first connection site 101 is split into two flows (by means of the first and the second main lines 107a, 107b) that are separate from each other and that rejoin near the outlet of the secondary line 111. In some embodiments, dividing and rejoining the flow of fluid into the insert piece 110 using the two separate main line 107a, 107b generated turbulences within the fluid flowing through the insert piece 100.

As can be seen from FIG. 1, the first and the second main lines 107a, 107b can be advantageously arranged such that the two flows collide or meet in a more or less frontal direction.

FIG. 2 shows a section view of the insert piece 100 of FIG. 1 along a first cut plane in the longitudinal direction in a plan view.

FIG. 3 shows a section view the insert piece 100 of FIG. 1 along a second plane perpendicular to the first plane of FIG. 2.

As can be seen from FIG. 3, in any embodiment according to the present invention—such as the one shown in FIG. 3 without being limited to this particular embodiment the secondary line 111 and/or the third connection site 105 may be perpendicular to the plane in which the first and the second main lines 107a, 107b extend, the plane being in a horizontal or left-right direction in FIG. 3. However, as depicted in FIGS. 1 and 3, the plane parallel to the outlet opening 115 of the secondary line 111, through which the second fluid exits in order to mix with the first fluid in the insert piece 100, can be perpendicular to the plane in which the first and the second main lines 107a, 107b extend. Alternatively, the direction along which the second fluid exits from the secondary line 111 in order to mix with the first fluid may be parallel to or part of the plane in which the first and the second main lines 107a, 107b extend.

Hence, the second fluid provided by the secondary line 111 has to change its travelling direction (indicated in FIG. 3 in a broken line) upon exiting the outlet opening 115 of the secondary line 111 in order to enter into the first fluid in the insert piece 100.

Figure 4:
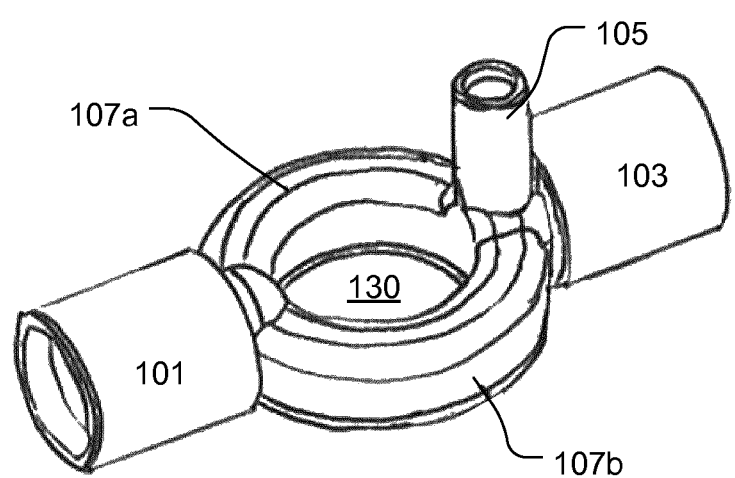
FIG. 4 shows an insert piece in a second exemplary embodiment.

FIG. 4 shows the insert piece 100 in a second exemplary embodiment.

The first main line 107a and the second main line 107b of the second exemplary embodiment depicted in FIG. 4 are integrally formed parts of the insert piece 100. In some embodiments, the first main line 107a and the second main line 107b are made from the same material as, for example, the first connection site 101, which facilitates the production process of the insert piece 100. The insert piece 100 can be formed by injection molding.

Figure 5:
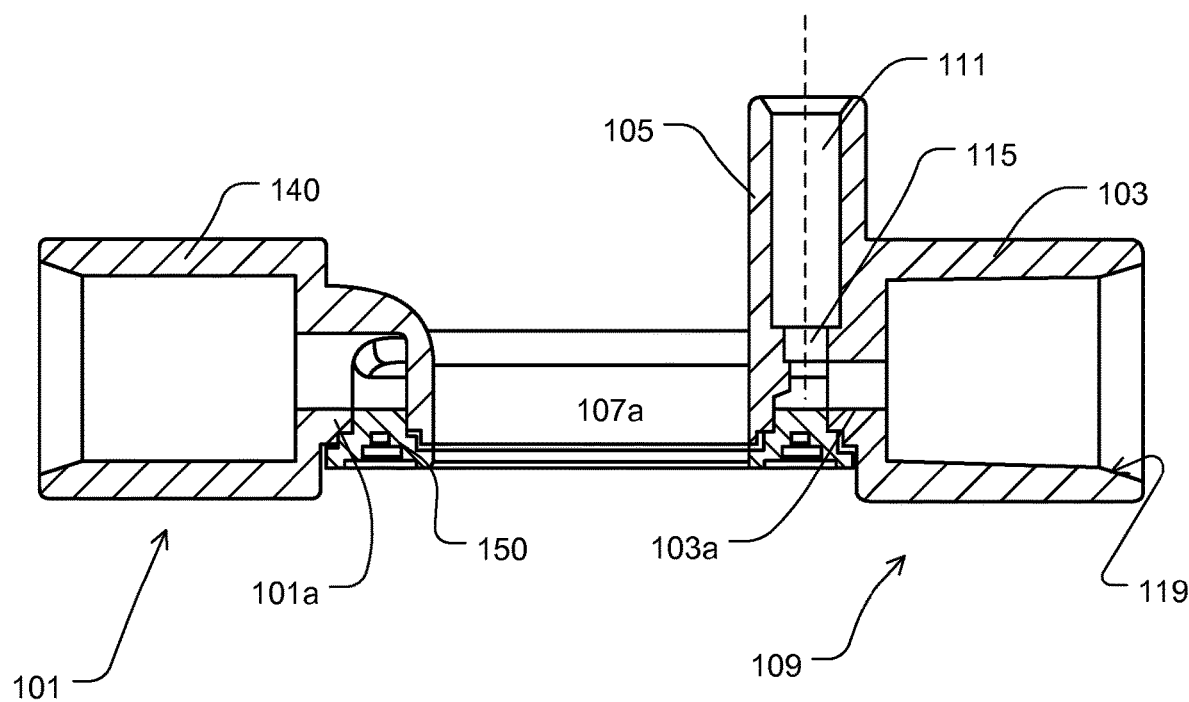
FIG. 5 shows a cross sectional view of an insert piece similar to that of FIG. 4.

FIG. 5 shows a section view of an insert piece 100 similar to that of FIG. 4 along a first plane.

FIG. 5 depicts an entrance 101a into the first main line 107a and/or into the second main line 107b. The entrance 101a can be either part of the first connection site 101 or the first and/or second main lines 107a, 107b.

FIG. 5 also depicts an exit 103a from the first main line 107a and/or from the second main line 107b. The exit 103a can be either part of the second connection site 103 or the first and/or second main lines 107a, 107b.

The presence of an entrance 101a and/or an exit 103a and their designs as discussed above, are not limited to the embodiment shown in FIG. 5.

As is shown in FIG. 5, the insert piece 100 can include an upper part 140 and a lower part 150, The upper part 140 and the lower part 150 of the insert piece 100 can be glued to one another or connected to each other in any other way (such as welding).

As can be seen from FIG. 5, in any embodiment according to the present invention—such as the one shown in FIG. 5 without being limited to this particular embodiment—the secondary line 111 and/or its third connection site 105 can be perpendicular to the plane along which the first and the second main lines 107a, 107b extend, the plane being in a horizontal or left-right direction in FIG. 5. The opening plane (or mouth) of the secondary line 111, through which the second fluid exits in order to mix with the first fluid can be parallel to the plane along which the first and the second main lines 107a, 107b extend. Alternatively, the direction along which the second fluid exits from the secondary line 111 in order to mix with the first fluid can be perpendicular to the plane along which the first and the second main lines 107a, 107b extend. Hence, inside of the mouth piece of the secondary line 111 the second fluid provided by the secondary line does not have to change its direction of travel (indicated in FIG. 5 in a broken line) in order to exit from the secondary line 111 and to enter into the first fluid in the insert piece.

Figure 6:
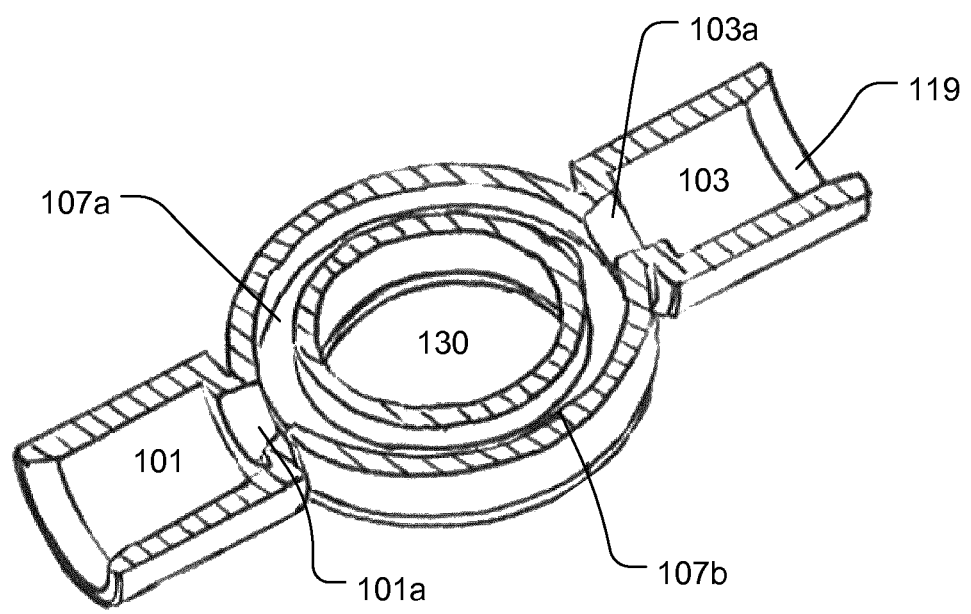
FIG. 6 shows a cross sectional view of a lower part of the insert piece of FIG. 4.

FIG. 6 shows section view of a first portion of the insert piece 100 of FIG. 4 along a second plane perpendicular to the first plane of FIG. 2.

Also, as can be seen from FIG. 6, in any embodiment according to the present invention—such as the one shown in FIG. 6 without being limited to this particular embodiment—the first and the second main lines 107a, 107b can be arranged such that they form a circular through-opening 130 within a plane extending through the first and the second main lines 107a, 107b.

Figure 7:
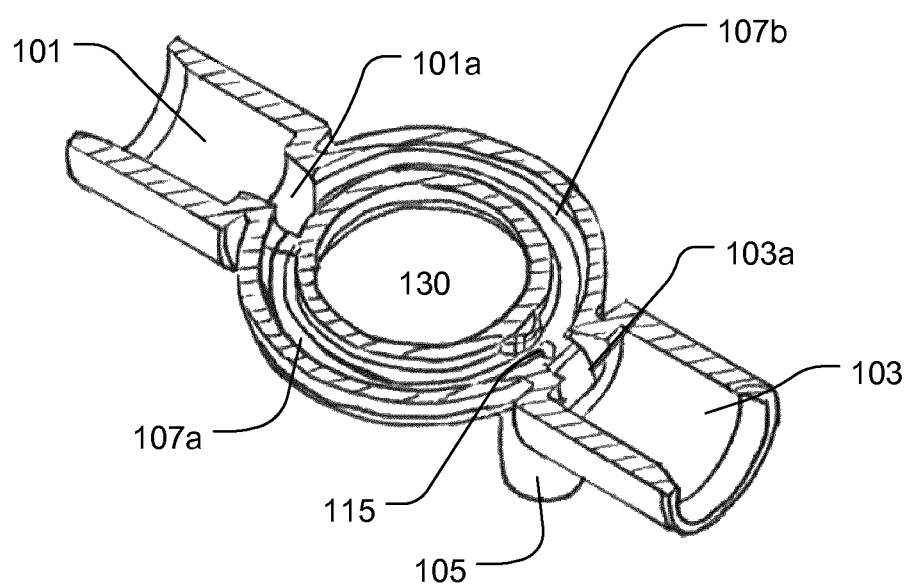
FIG. 7 shows a cross sectional view of an upper part of the insert piece of FIG. 4.

FIG. 7 shows a section view of a second portion of the insert piece 100 along the second plane perpendicular to the first plane of FIG. 2.

In the embodiment shown in FIG. 7, the cross sectional area of the first main line 107a and/or the cross sectional of the second main line 107b is less than half of the cross sectional area of the first connection site 101 and/or of the second connection site 103.

For example, the first connection site 101 may have a cross sectional area of about 14.51 mm$^2$ (at a diameter of 4.3 mm) whereas the cross sectional area of the first main line 107a and/or the cross section of the second main line 107b may be about 2.83 mm$^2$ (at a diameter of 1.9 mm). Other values for the cross section area of the first main line 107a and/or the cross section of the second main line 107b, such as 3.14 mm$^2$ (at a diameter of 2.0 mm) are within the scope of this disclosure.

Figure 8:
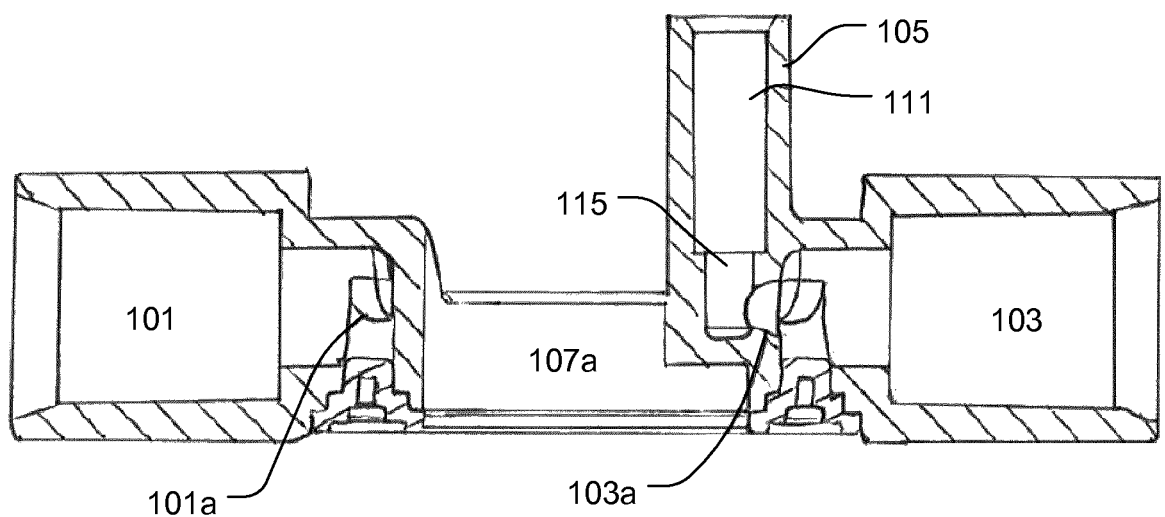
FIG. 8 shows a cross sectional view of an insert piece according to a third exemplary embodiment.

FIG. 8 shows a section view of the insert piece 100 in a third exemplary embodiment along a first plane.

Figure 9:
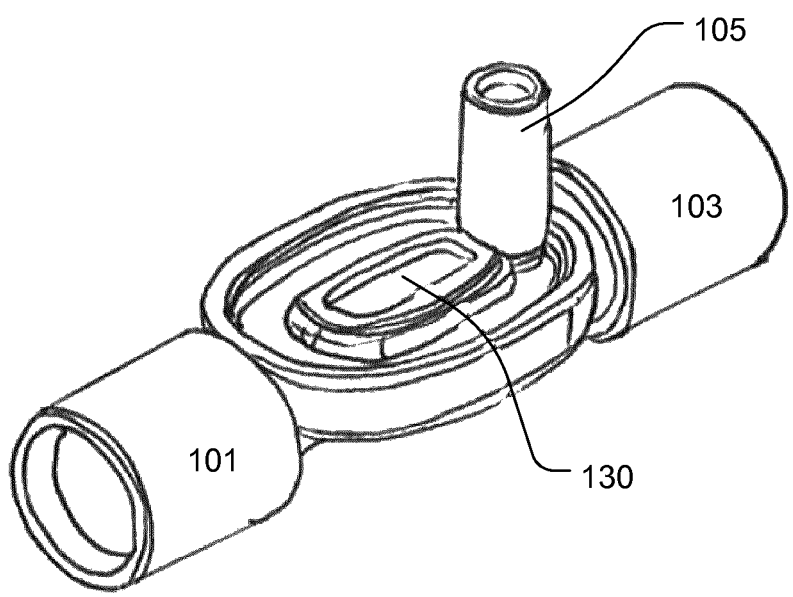
FIG. 9 shows a partly cut insert piece according to a fourth exemplary embodiment.

FIG. 9 shows a partially cut insert piece 100 in a fourth exemplary embodiment.

In contrast to the insert piece 100 of depicted in FIGS. 1 to 3, the through-opening 130 of the insert piece 100 depicted in FIG. 9 is oval in shape.

Figure 10:
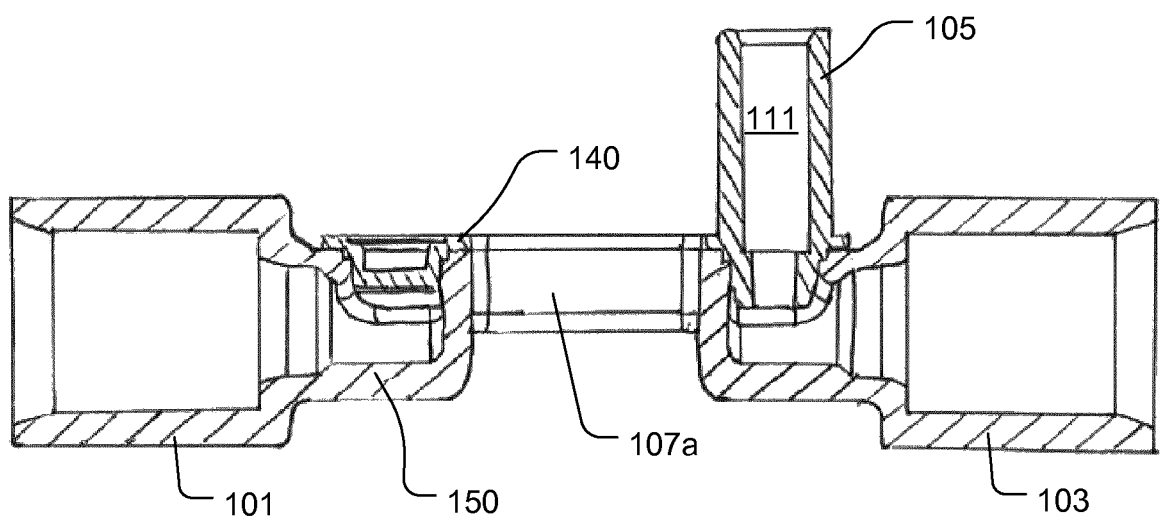
FIG. 10 shows a cross sectional view of the insert piece of FIG. 9.

FIG. 10 shows a section view of the insert piece 100 of FIG. 9 along a plane.

FIG. 11 shows an exemplary embodiment of an arrangement of an insert piece 100 as described herein in an extracorporeal blood tubing set 200 according to the present invention.

As depicted in FIG. 11, the blood tubing set 200 includes or is connected to a hemofilter 201. A blood withdrawal line 203 (or arterial line) and a blood return line 205 (or venous line) are connected to the hemofilter 201 or dialyzer or blood filter.

The blood withdrawal line 203 is operatively connected to, or includes, a blood pump 301.

In some embodiments, an addition line 207 for citrate solution opens upstream of the blood pump 301 into the blood withdrawal line 203.

The line 207 is operatively connected to, or includes, a citrate pump 307.

Downstream of the hemofilter 201, the line 209 for calcium solution opens into the blood return line 205.

The insert piece 100 is operatively connected to a calcium pump 309. The calcium pump is supplied by a source for infusion solution which is not shown in FIG. 11, such as a calcium source. The source may be a bag or a bottle. The infusion solution may optionally be generated on-line, and the respective device generating the solution on-line is considered as a source.

The operative connection to the calcium pump 309 is to be understood herein as an example. In some implementations, the insert piece 100 is arranged behind another pump other than a calcium pump, for example downstream of a citrate pump like the citrate pump 307 of FIG. 11.

The hemofilter 201 is connected to a line 311 for fresh dialysis liquid and to a line 315 for spent dialysate or filtrate. The line 311 is connected to, or includes, a dialysis liquid pump 313. The line 315 is connected to, or includes, a filtrate pump 317.

The arrow in FIG. 11 indicates the flow direction through the blood tubing set 200.

The blood tubing set 200 shown in FIG. 11 may correspond to a standard extracorporeal blood tubing set and may in particular be suitable for the CVVHD (continuous venovenous hemodialysis).

The pumps 301, 307, 309, 313 and 317 and the lines 311 and 315 may be part of a blood treatment apparatus 300.

Figure 12:
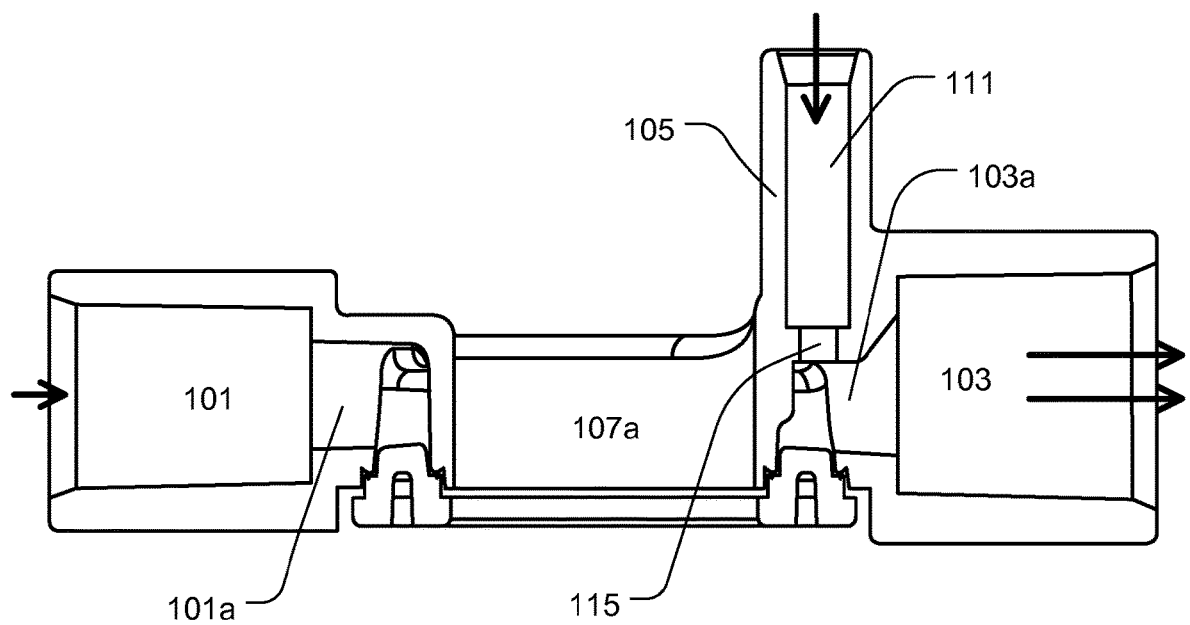
FIG. 12 shows a cross sectional view of an insert piece according to a fifth exemplary embodiment.

FIG. 12 shows a longitudinal cross section of an insert piece 100 according to a fifth exemplary embodiment. The arrows indicate the flow directions into or out of the insert piece 100, either of the blood or calcium solution or a mixture thereof during use of the insert piece 100.

In some embodiments, and in particular in the embodiment shown in FIG. 12, the diameter or cross sectional area of the first connection site 101 (that can be suitable for a 3.5×5.5 mm tube) of the insert piece 100 is less than, or equal to, the diameter or cross sectional area of the second connection site 103 (that can be suitable for a 4.3×6.8 mm tube). An enlarged lumen closely downstream the connection of the secondary line 111 can be used to decelerate the speed of the flow and, therefore, advantageously allow a more thorough mixing.

Figure 13A:
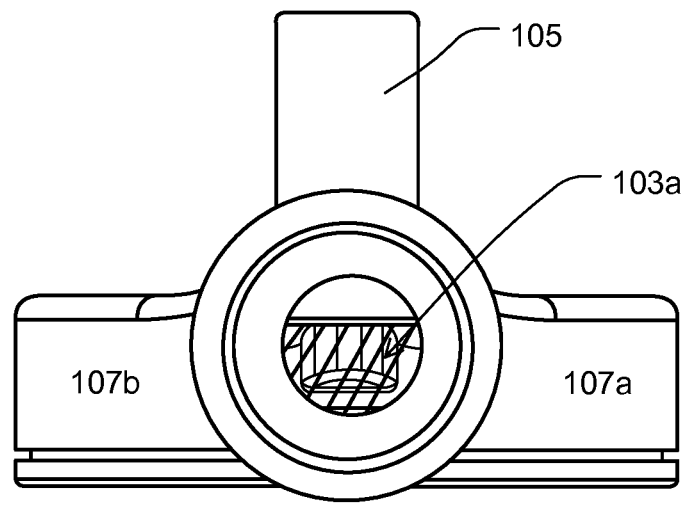
FIG. 13a shows a rear view of the insert piece of FIG. 12.

FIG. 13a shows a rear view of the insert piece 100 of FIG. 12.

Figure 13B:
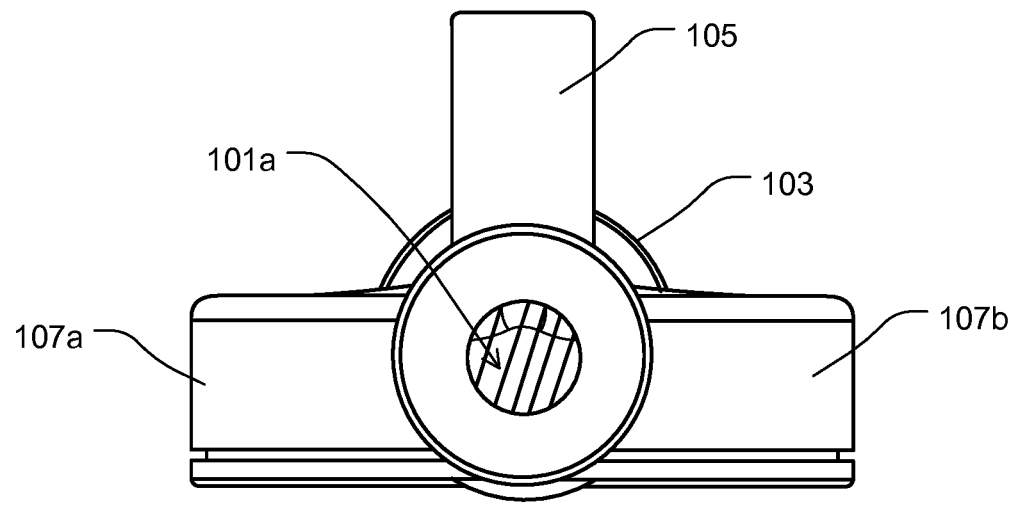
FIG. 13b shows a front view of the insert piece of FIG. 12.

It can be seen that the circular exit 103a has a larger diameter than the circular entrance 101a shown in FIG. 13b.

FIG. 13b shows a front view of the insert piece 100 of FIG. 12.

As can be seen in FIGS. 13a and 13b, the circular exit 103a has a larger diameter than the circular entrance 101a shown in FIG. 13b.

LIST OF REFERENCE NUMERALS 100 insert piece
101 first connection site
101a entrance
103 second connection site
103a exit
105 third connection site
107a first main line
107b second main line
109 junction portion or connection portion
111 secondary line
115 outlet opening or outlet
119 chamfer
130 through-opening
140 upper part of insert piece
150 lower part of insert piece
200 blood tubing set, blood tubing system
201 hemofilter or blood filter or dialyzer
203 blood withdrawal line
205 blood return line
205a first tubing portion
205b second tubing portion
207 line for citrate solution
209 line for calcium solution; addition line; third tubing portion
300 blood treatment apparatus
301 blood pump
307 citrate pump
309 calcium pump
311 line for fresh dialysis liquid
313 pump for fresh dialysis liquid
315 line for spent dialysate, or filtrate
317 pump for spent dialysate, or filtrate
H flow direction of the first fluid into and through the first main line
B flow direction of the first fluid into and through the second main line
N inflow direction of the second fluid into the secondary line

The invention claimed is:

1. An insert piece for a blood tubing set, the insert piece comprising:
　a first connection site configured to couple to a first tubing portion of the blood tubing set;
　a second connection site configured to couple to a second tubing portion of the blood tubing set;
　a third connection site configured to couple to a third tubing portion of the blood tubing set;
　a first main line configured to conduct a first liquid through the insert piece, wherein the first main line is fluidly coupled to the first connection site and the second connection site;
　a second main line configured for conducting the first liquid through the insert piece, wherein the second main line is fluidly coupled to the first connection site and the second connection site; and
　a secondary line configured to conduct a second liquid into at least one of the first main line, the second main line, or a connection portion connecting the first main line and the second main line to each other or to the second connection site, wherein:
　　the secondary line is fluidly coupled to the third connection site;
　　the first connection site comprises a perfusable lumen having a first cross sectional area;
　　the second connection site comprises a perfusable lumen having a second cross sectional area;
　　at least one of the first main line and/or the second main line comprises a perfusable lumen having a third cross sectional area; and
　　at least one of the first main line, the second main line, a portion of the first main line, or a portion of the second main line is a tube inserted into a tube intake in fluid communication with the first connection site or with the second connection site.

2. The insert piece of claim 1, wherein a sum of a first cross sectional area of the first main line and a second cross sectional area of the second main line is smaller than at least one of a cross sectional area of the first connection site, a cross sectional area of the second connection site, or a cross sectional area of a tube section of the blood tubing set.

3. The insert piece of claim 1, wherein the secondary line is in fluid communication with a source of infusion solution.

4. The insert piece of claim 1, wherein the third cross sectional area is substantially half as large as at least one of the first cross sectional area or the second cross sectional area.

5. The insert piece of claim 1, wherein the third cross sectional area is less than half as large as at least one of the first cross sectional area or the second cross sectional area.

6. The insert piece of claim 1, wherein the connection portion is arranged along a flow direction of the first liquid between at least one of the first main line or the second main line on a first side and at least one of the second connection site or the third connection site on a second side.

7. The insert piece of claim 1, wherein the connection portion comprises a cross section in a flow direction towards the second connection site that widens or enlarges along the flow direction.

8. The insert piece of claim 1, wherein a longitudinal axis of the connection portion is perpendicular to a longitudinal axis of the secondary line.

9. The insert piece of claim 1, further comprising a through-opening arranged between the first main line and the second main line.

10. The insert piece of claim 1, wherein the insert piece comprises two or more components welded or glued to each other.

11. The insert piece of claim 1, wherein at least one of the first main line or the second main line is an integral part of the insert piece.

12. The insert piece of claim 1, wherein the first liquid comprises blood.

13. The insert piece of claim 1, wherein the second liquid comprises an infusion solution.

14. A blood tubing set comprising:
at least one insert piece comprising:
a first connection site configured to couple to a first tubing portion of the blood tubing set;
a second connection site configured to couple to a second tubing portion of the blood tubing set;
a third connection site configured to couple to a third tubing portion of the blood tubing set;
a first main line configured to conduct a first liquid through the insert piece, wherein the first main line is fluidly coupled to the first connection site and the second connection site;
a second main line configured for conducting the first liquid through the insert piece, wherein the second main line is fluidly coupled to the first connection site and the second connection site; and
a secondary line configured to conduct a second liquid into at least one of the first main line, the second main line, or a connection portion connecting the first main line and the second main line to each other or to the second connection site;
an addition line;
a blood withdrawal line; and
a blood return line; wherein:
the at least one insert piece is fluidly coupled to at least one of the addition line, the blood withdrawal line, or the blood return line;
the secondary line is fluidly coupled to the third connection site;
the first connection site comprises a perfusable lumen having a first cross sectional area;
the second connection site comprises a perfusable lumen having a second cross sectional area;
at least one of the first main line and/or the second main line comprises a perfusable lumen having a third cross sectional area; and
at least one of the first main line, the second main line, a portion of the first main line, or a portion of the second main line is a tube inserted into a tube intake in fluid communication with the first connection site or with the second connection site.

15. The blood tubing set of claim 14, wherein the blood tubing set is configured to execute a regional anticoagulation.

16. The blood tubing set of claim 14, wherein the blood tubing set is configured to execute at least one of a hemodialysis treatment, a hemofiltration treatment, a hemodiafiltration treatment, a plasmapheresis treatment, or a whole blood adsorption treatment.

17. The blood tubing set of claim 14, wherein:
the first connection site and the second connection site are each fluidly coupled to the blood return line; and
the third connection site is fluidly coupled to the addition line.

18. The blood tubing set of claim 17, wherein the addition line is a calcium line.

19. A system comprising:
a blood treatment apparatus; and
a blood tubing set coupled to the blood treatment apparatus, wherein the blood tubing set comprises:
at least one insert piece comprising:
a first connection site configured to couple to a first tubing portion of the blood tubing set
a second connection site configured to couple to a second tubing portion of the blood tubing set;
a third connection site configured to couple to a third tubing portion of the blood tubing set;
a first main line configured to conduct a first liquid through the insert piece, wherein the first main line is fluidly coupled to the first connection site and the second connection site;
a second main line configured for conducting the first liquid through the insert piece, wherein the second main line is fluidly coupled to the first connection site and the second connection site; and
a secondary line configured to conduct a second liquid into at least one of the first main line, the second main line, or a connection portion connecting the first main line and the second main line to each other or to the second connection site;
an addition line;
a blood withdrawal line; and
a blood return line, wherein:
the at least one insert piece is fluidly coupled to at least one of the addition line, the blood withdrawal line, or the blood return line;
the secondary line is fluidly coupled to the third connection site;
the first connection site comprises a perfusable lumen having a first cross sectional area;
the second connection site comprises a perfusable lumen having a second cross sectional area;
at least one of the first main line and/or the second main line comprises a perfusable lumen having a third cross sectional area; and
at least one of the first main line, the second main line, a portion of the first main line, or a portion of the second main line is a tube inserted into a tube intake in fluid communication with the first connection site or with the second connection site.

* * * * *

UNITED STATES PATENT AND TRADEMARK OFFICE
CERTIFICATE OF CORRECTION

| | |
|---|---|
| PATENT NO. | : 11,707,561 B2 |
| APPLICATION NO. | : 16/625577 |
| DATED | : July 25, 2023 |
| INVENTOR(S) | : Davide Maria Benelli, Massimo Earl Fini and Reinhold Reiter |

It is certified that error appears in the above-identified patent and that said Letters Patent is hereby corrected as shown below:

In the Claims

Column 16, Line 17, in Claim 19, delete "set" and insert --set;--.

Signed and Sealed this
Twelfth Day of September, 2023

Katherine Kelly Vidal
*Director of the United States Patent and Trademark Office*